Jan. 19, 1960 E. S. BOERNER Plant Pat. 1,900
ROSE PLANT
Filed May 25, 1959
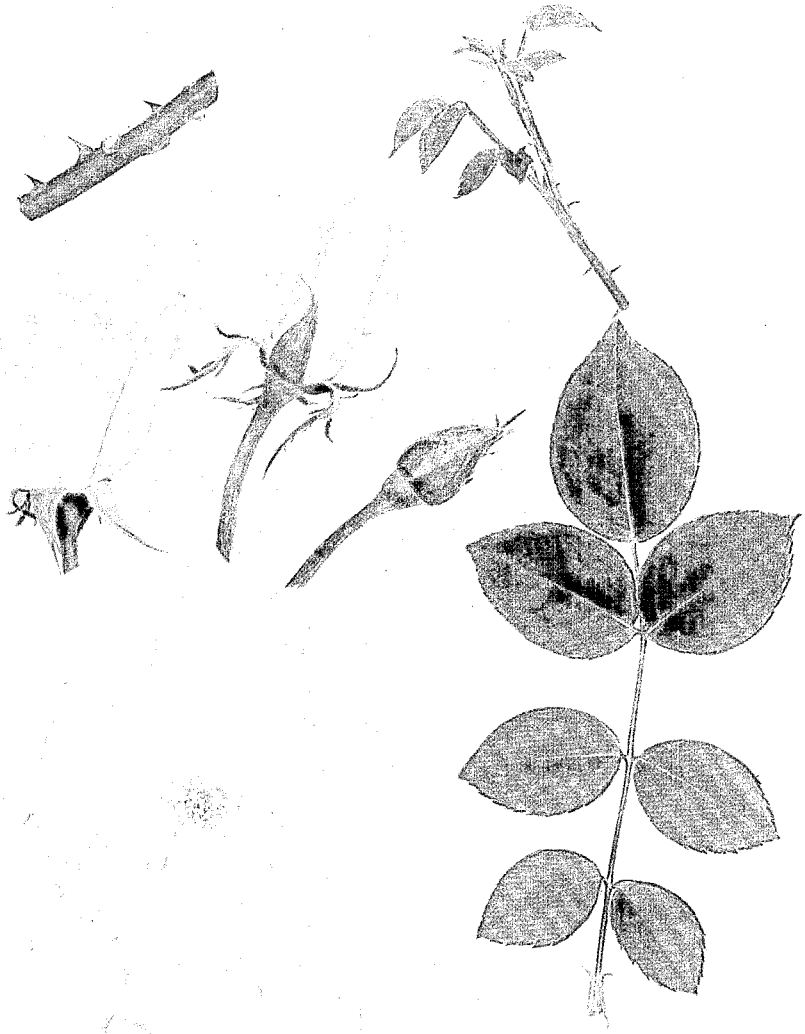
Inventor.
E. S. Boerner
By: Robb & Robb
Attorneys.

United States Patent Office

Plant Pat. 1,900
Patented Jan. 19, 1960

1,900

ROSE PLANT

Eugene S. Boerner, Newark, N.Y., assignor to Jackson & Perkins Company, Newark, N.Y., a corporation of New York Application May 25, 1959, Serial No. 815,759

1 Claim. (Cl. 47—61)

The present invention relates to a new and distinct variety of rose plant of the hybrid tea class, which was originated by me by crossing the variety "Golden Masterpiece" (Plant Patent No. 1284) with the variety "Tawny Gold" (Plant Patent No. 950).

The primary objective of this breeding was to produce a new rose variety similar to that of the parent "Golden Masterpiece," but with flowers of superior fragrance. This objective was fully achieved, along with other desirable improvements, as evidenced by the following unique combination of characteristics which are outstanding in the new variety and which distinguish it from its parents, as well as from all other varieties of which I am aware:

(1) A vigorous habit of growth;

(2) A strong flower fragrance corresponding to "Old Rose perfume" (centifolia); and (3) A distinctive general color tonality of the flowers, corresponding to Cartridge Buff, lightly overcast with Eosine Pink, and with Cadmium Orange at the base of the petals.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgeway's Color Standards and Nomenclature:

Parentage: Seedling.
*Seed parent.*—"Golden Masterpiece."
*Pollen parent.*—"Tawny Gold."

Classification:
*Botanic.*—Hybrid tea.
*Commercial.*—Hybrid tea.

*Flower*

(Observations made from specimens grown in a greenhouse at Newark, New York in the early morning during the middle of January.)

Blooming habit: Recurrent—continuous.

Bud:
*Size.*—*Medium.*
*Form.*—Long pointed; is not affected by wet or hot weather.
*Color.*—When sepals first divide—Alizarine Pink, Plate 13. When petals begin to unfurl—Carrot Red, Plate 14, lightly overcast with Flesh color, Plate 14. When half-blown: inside of petals—Cartridge Buff, Plate 30, lightly overcast with Orient Pink, Plate 2; reverse of petals—Maize Yellow, Plate 4, with edges of petals lightly overcast with Light Jasper Red, Plate 13.
*Sepals.*—Branched ("hood" above bud); curl back when petals begin to unfurl. Color: inside—Pale Turtle Green, Plate 32; outside—Light Bice Green, Plate 17.
*Calyx.*—Color—Light Bice Green, Plate 17. Shape—funnel. Size—long. Aspect—smooth. Odor when rubbed—none.
*Peduncle.* — Length — long. Aspect — rough. Strength—stiff; heavy. Color—Oil Green, Plate 5.
*Opening.*—Opens up well; is not affected by adverse weather conditions.

Bloom:
*Size.*—Large. Average size when fully expanded—4½ inches.
*Borne.*—Both singly and several together.
*Stems.*—Long; strong.
*Form (when first open).*—High-center. Permanence—retains its form to the end.
*Petalage.*—Double (full but open center). Number of petals under normal conditions—from 55 to 60.
*Color.*—Center of flower—Eosine Pink, Plate 1, lightly overcast with Orient Pink, Plate 2. Outer petals—Ivory Yellow, Plate 30, very lightly overcast with Eosine Pink, Plate 1 on the outer edge of the petals. Base of petals (aiglet)—Cadmium Orange, Plate 3. Inside of petals—Cartridge Buff, Plate 30, lightly overcast with Eosine Pink, Plate 1. Reverse of petals—Ivory Yellow, Plate 30, lightly overcast with Pale Pinkish Buff, Plate 29. General tonality from a distance—Cartridge Buff, Plate 30, lightly overcast with Eosine Pink, Plate 1.
*Discoloration.*—General tonality at end of first day—Cartridge Buff, Plate 30, lightly overcast with Eosine Pink, Plate 1. Second day—Cartridge Buff, Plate 30, lightly overcast with Eosine Pink, Plate 1. Third day—Cartridge Buff, Plate 30, very lightly overcast with Eosine Pink, Plate 1.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Many; large.
*Persistence.*—Drop off cleanly.
*Fragrance.*—Strong. Nature—"Old Rose perfume" (centifolia).
*Lasting quality.*—On the plant—very long. As cut flower—very long.

*Genital organs*

Stamens, anthers: Large; many; regularly arranged around styles. Color—Capucine Yellow, Plate 3.
Stamens, filaments (threads): Medium length. Color—Pinard Yellow, Plate 4.
Pollen: Color—Pale Yellow-orange, Plate 3.
Styles: Loosely separated; uneven length; medium length; thin.
Stigmas: Color—Baryta Yellow, Plate 4.
Ovaries: All enclosed in calyx.
Hips: None.
Seeds: None.

*Plant*

Form: Bush.
Growth: Vigorous; upright.

Foliage: Compound of 3 to 7 leaflets.

*Size.*—Medium.

*Quantity.*—Normal.

*Color.*—New foliage: Upper side—Oil Green, Plate 5, lightly overcast with Oxblood Red, Plate 1, with serrations of Oxblood Red, Plate 1; under side—Yellowish Oil Green, Plate 5, lightly overcast with Van Dyke Red, Plate 1. Old foliage: upper side—Dark Dull Yellow-Green, Plate 32; under side—Light Bice Green, Plate 17.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; small.

*Leaf stem.*—Color—Light Bice Green, Plate 17. Under side—prickly.

*Stipules.*—Medium length; bearded.

Wood:

*New wood.*—Color—Yellowish Citrine, Plate 16. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium lengths; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous habit of growth, a strong flower fragrance corresponding to "Old Rose perfume" (centifolia), and a distinctive Cartridge Buff, lightly overcast with Eosine Pink general color tonality of the flowers, with Cadmium Orange color at the base of the flower petals.

No references cited.